(12) United States Patent
Cai et al.

(10) Patent No.: US 12,048,573 B2
(45) Date of Patent: Jul. 30, 2024

(54) SYSTEMS FOR X-RAY IMAGING

(71) Applicant: GE Precision Healthcare LLC, Milwaukee, WI (US)

(72) Inventors: Changliang Cai, Beijing (CN); Chang Wang, Beijing (CN); Da Sheng, Beijing (CN)

(73) Assignee: GE Precision Healthcare LLC, Milwaukee, WI (US)

( * ) Notice: Subject to any disclaimer, the term of this patent is extended or adjusted under 35 U.S.C. 154(b) by 448 days.

(21) Appl. No.: 17/453,812

(22) Filed: Nov. 5, 2021

(65) Prior Publication Data
US 2023/0144883 A1 May 11, 2023

(51) Int. Cl.
*A61B 6/00* (2024.01)
*A61B 6/06* (2006.01)

(52) U.S. Cl.
CPC .............. *A61B 6/4441* (2013.01); *A61B 6/06* (2013.01); *A61B 6/56* (2013.01)

(58) Field of Classification Search
CPC .................................................. A61B 6/4441
See application file for complete search history.

(56) References Cited

U.S. PATENT DOCUMENTS 10,568,592 B2    2/2020  Jung
2019/0221046 A1*  7/2019 Maeda ................. A61B 6/5264

FOREIGN PATENT DOCUMENTS

CN         104185352 B      2/2017

* cited by examiner

*Primary Examiner* — Dani Fox

(57) ABSTRACT

Various systems are provided for medical imaging systems. In one example, an assembly for a C-arm comprises: a casing including a first extension housing a first component, a second extension housing a second component, and a clearance formed between the first extension and the second extension; and a collimator seated within the clearance, with an outlet end of the collimator substantially aligned with a terminating end of the first extension and a terminating end of the second extension. An x-ray tube insert may be aligned with the collimator and configured to emit x-ray radiation between the first component and the second component.

20 Claims, 6 Drawing Sheets

SYSTEMS FOR X-RAY IMAGING

FIELD

Embodiments of the subject matter disclosed herein relate to medical imaging systems, and more particularly, to radiographic imaging systems.

BACKGROUND

Radiographic imaging systems may be used in various applications, including medical and industrial applications. In a medical environment, a radiographic imaging device may provide a non-invasive means of imaging tissue and bone of a patient. The imaging device may have the capability of capturing multiple images at designated intervals and displaying the images in a sequence to create a single image of the object being examined.

The imaging device may comprise a C-arm coupled to a base unit. The C-arm may include an x-ray source positioned at one end of the arm and a detector positioned at another end of the arm. A clearance may be provided between the x-ray source and the detector to receive an object, such as a portion of the patient's body, which may be irradiated with radiation from the x-ray source. Upon irradiating the object, the x-ray radiation penetrates through the object and is captured by the detector. By penetrating the object placed between the source and detector, the x-rays enable an image of the object to be captured and relayed to the display monitor, where the image may be displayed or stored and retrieved later.

BRIEF DESCRIPTION

In one example, an assembly for a C-arm comprises: a casing including a first extension housing a first component, a second extension housing a second component, and a clearance formed between the first extension and the second extension; and a collimator seated within the clearance, with an outlet end of the collimator substantially aligned with a terminating end of the first extension and a terminating end of the second extension.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 2-6 are shown approximately to scale, although other relative dimensions may be used, if desired.

DETAILED DESCRIPTION

Figure 3:
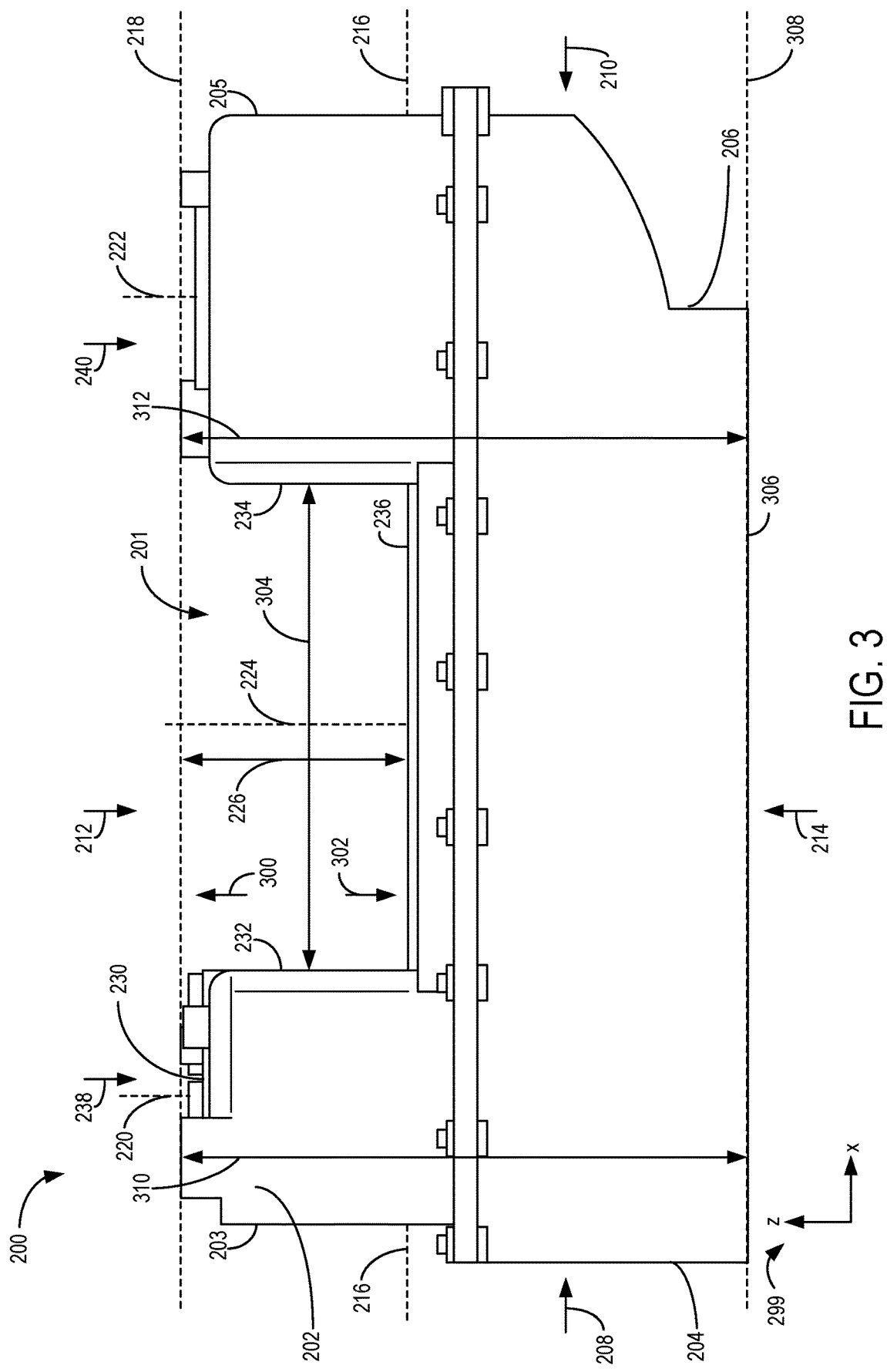
FIG. 3 shows a side view of the modular imaging assembly, according to an embodiment.
Figure 4:
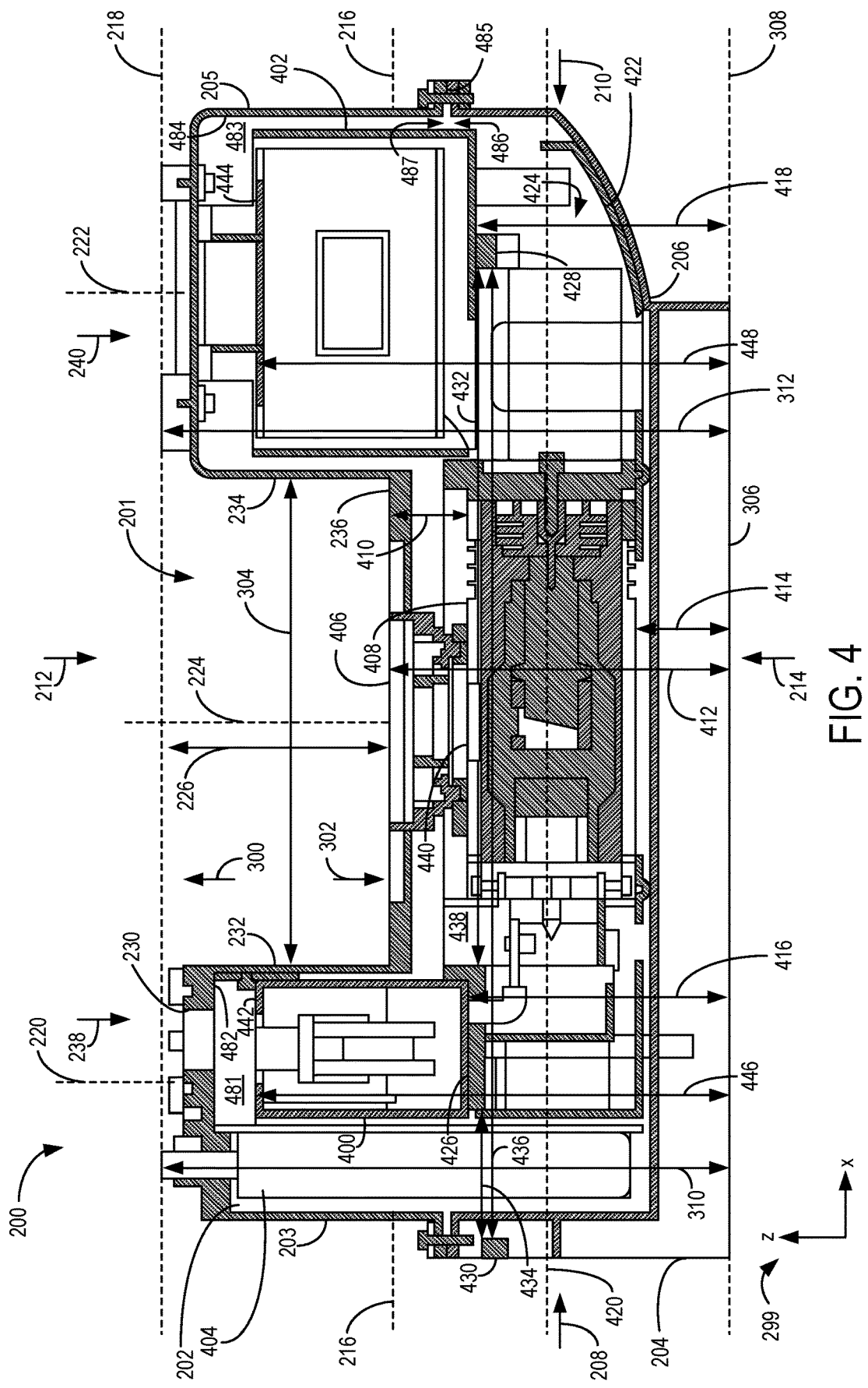
FIG. 4 shows a side sectional view of the modular imaging assembly, according to an embodiment.
Figure 5:
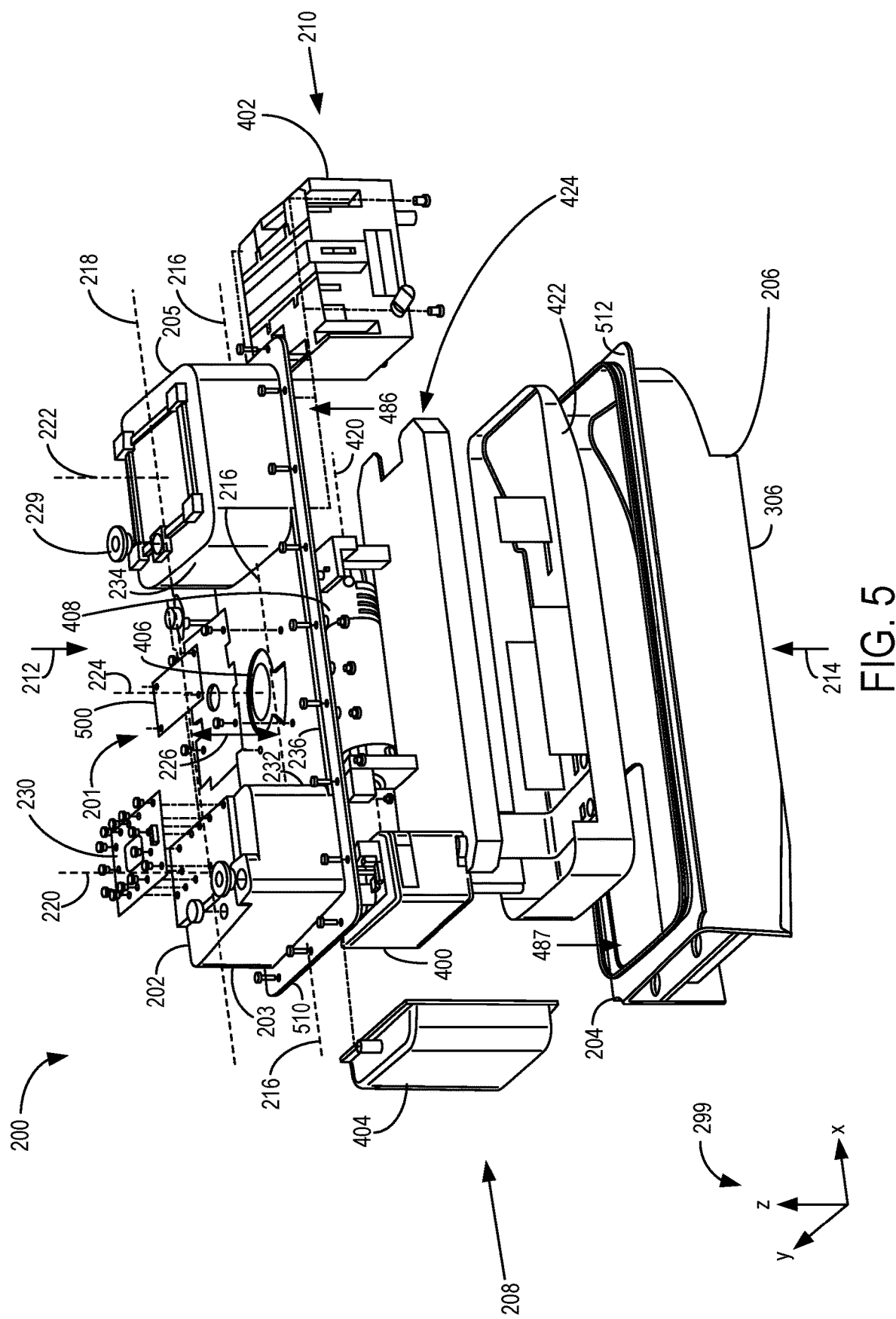
FIG. 5 shows an exploded view of the modular imaging assembly, according to an embodiment.
Figure 6:
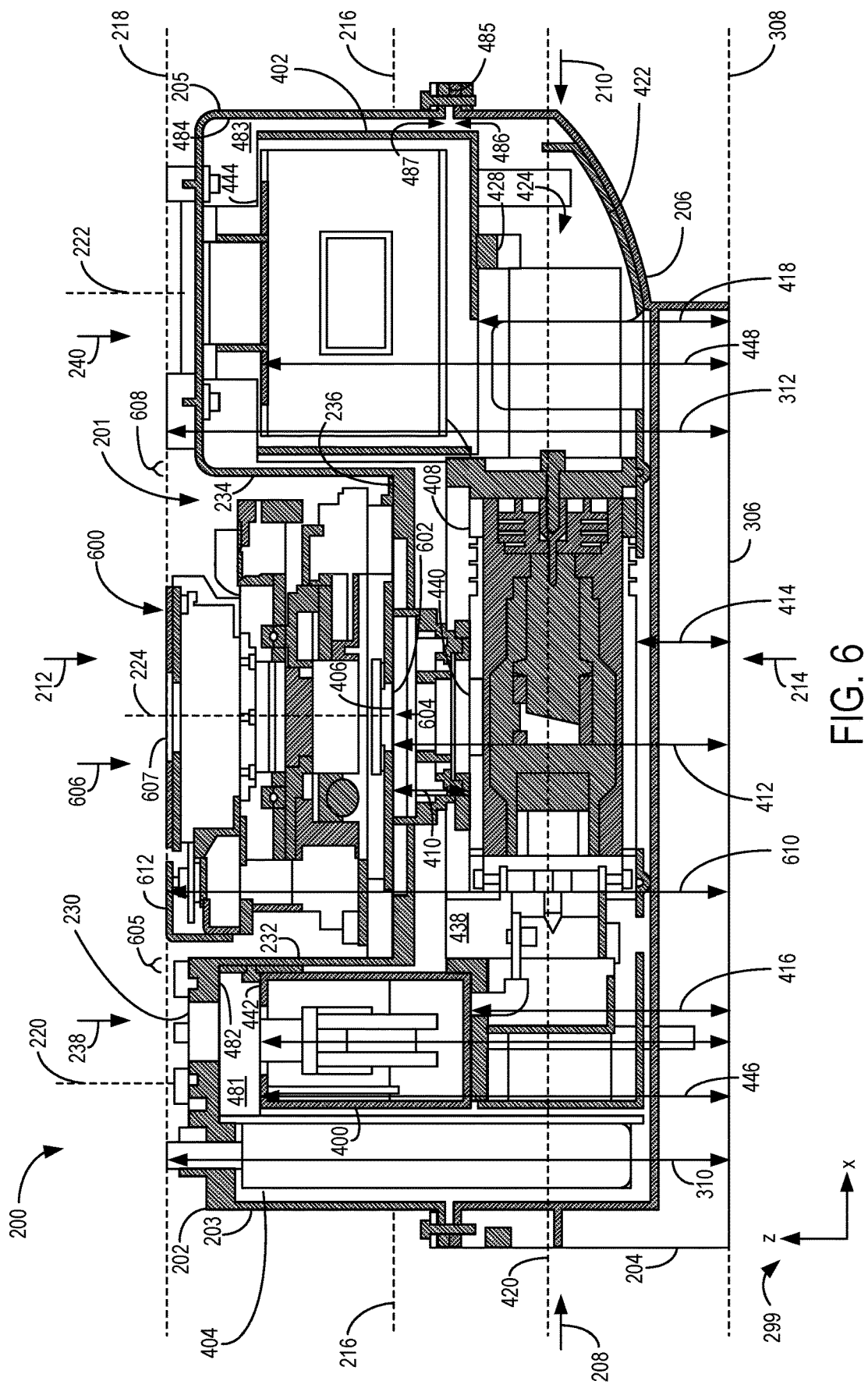
FIG. 6 shows a side sectional view of the modular imaging assembly with a collimator of the assembly seated in a recessed configuration, according to an embodiment.

The following description relates to various embodiments for medical imaging systems. A medical imaging system, such as the medical imaging system shown by FIG. 1, includes a modular imaging assembly, such as the modular imaging assembly shown by FIG. 2. The modular imaging assembly is configured to mount to a first end of a C-arm of the imaging system, opposite to an x-ray detector mounted to an opposing end of the C-arm. The modular imaging assembly may generate x-ray radiation that is received at the detector. An x-ray tube insert disposed within a casing of the modular imaging assembly, as shown by FIGS. 4-5, may be energized to generate x-ray radiation, with the x-ray radiation passing through a collimator seated within a clearance formed between opposing ends of the modular imaging assembly. The collimator collimates the x-ray radiation emitted by the x-ray tube insert and passes the collimated x-ray radiation to the detector for imaging of a subject arranged between the ends of the C-arm. The casing includes a recessed surface, as shown by FIG. 3, and the collimator is seated against the recessed surface, as shown by FIG. 6. By seating the collimator against the recessed surface, a size of the modular imaging assembly is reduced. As a result, an ease of use of the imaging system may be increased and a likelihood of contact of the modular imaging assembly with portions of a support device supporting the subject to be imaged may be reduced.

With the development of medical equipment, the C-arm has many usages in clinical applications such as orthopedics and vascular intervention. With the continuous deepening of the C-arm in clinical applications, the ease of C-arm operation has become a parameter of interest. Often, a conventional configuration of a C-arm imaging system includes an x-ray tube installed at the end of the C-arm, and a portion of the x-ray tube is located on the underside of the C-arm with a collimator mounted on top of the x-ray tube. However, such configurations can lead to potential problems. For example, such configurations can result in increased lateral height of the C-arm. As a result, a low height bench is often used to increase a height of the operator, but the bench may also increase operator discomfort. For ease of use it may be desirable to reduce the lateral height of the C-arm (e.g., to increase an ease of use of the C-arm during patient surgery), where the lateral height is the length of the C-arm in the direction from one end of the C-shaped portion of the C-arm to the opposing end of the C-shaped portion. Additionally, the table is often raised appropriately to increase a clearance between a cover or casing of the x-ray tube and the table, but this also increases the height at which the operator is positioned while using the C-arm during patient operations (e.g., surgery). Thus, it may also be desirable to reduce the total height of the collimator and the x-ray tube to increase the clearance between the cover of the x-ray tube and the table.

The assembly for a C-arm disclosed herein provides an internal horizontal modular layout, where a distance from a focus of an x-ray tube insert to a bottom of the assembly is smaller and a total height of tube and collimator is smaller relative to conventional configurations. The C-arm is thus provided a lower lateral height and a greater clearance between the cover of the x-ray tube and the patient support table, which may increase an ease of operation of the C-arm.

The internal components of the assembly may include a filament transformer, a high-voltage transformer (which may be referred to herein as a KV transformer), a high-voltage (HV) board, the x-ray tube insert, a bellows, etc. The filament transformer and the KV transformer may be distributed at both ends of the x-ray tube insert, the HV board may be mounted on the side of the filament transformer, and the HV board may be vertically mounted on the x-ray tube insert. The configuration disclosed herein may result in a smaller distance from the focus to the bottom of the x-ray tube insert, and the C-arm may obtain a lower lateral height. This may increase an ease of operation and ergonomic quality of the system. The configuration may result in a middle portion that is lower than the end portions. The collimator may be mounted at the middle position of the upper section of the casing, which may reduce a total height between the x-ray tube insert and the collimator, increase a clearance between the cover of the x-ray tube insert and the patient support table, and increase an ease of use of the system during clinical operations such as surgery. In addition, the modular design of the interior parts may increase an ease of assembly and/or disassembly of the modular imaging assembly. An arc-shape of a bottom section of the casing at one end may increase an ease of performing an overscan.

The concave shape of the upper box provides the installation location for collimator. The concave shape may reduce the total height of the assembly and the collimator and reduce the risk of collision between the cover of the x-ray tube insert and the patient support table.

Figure 1:
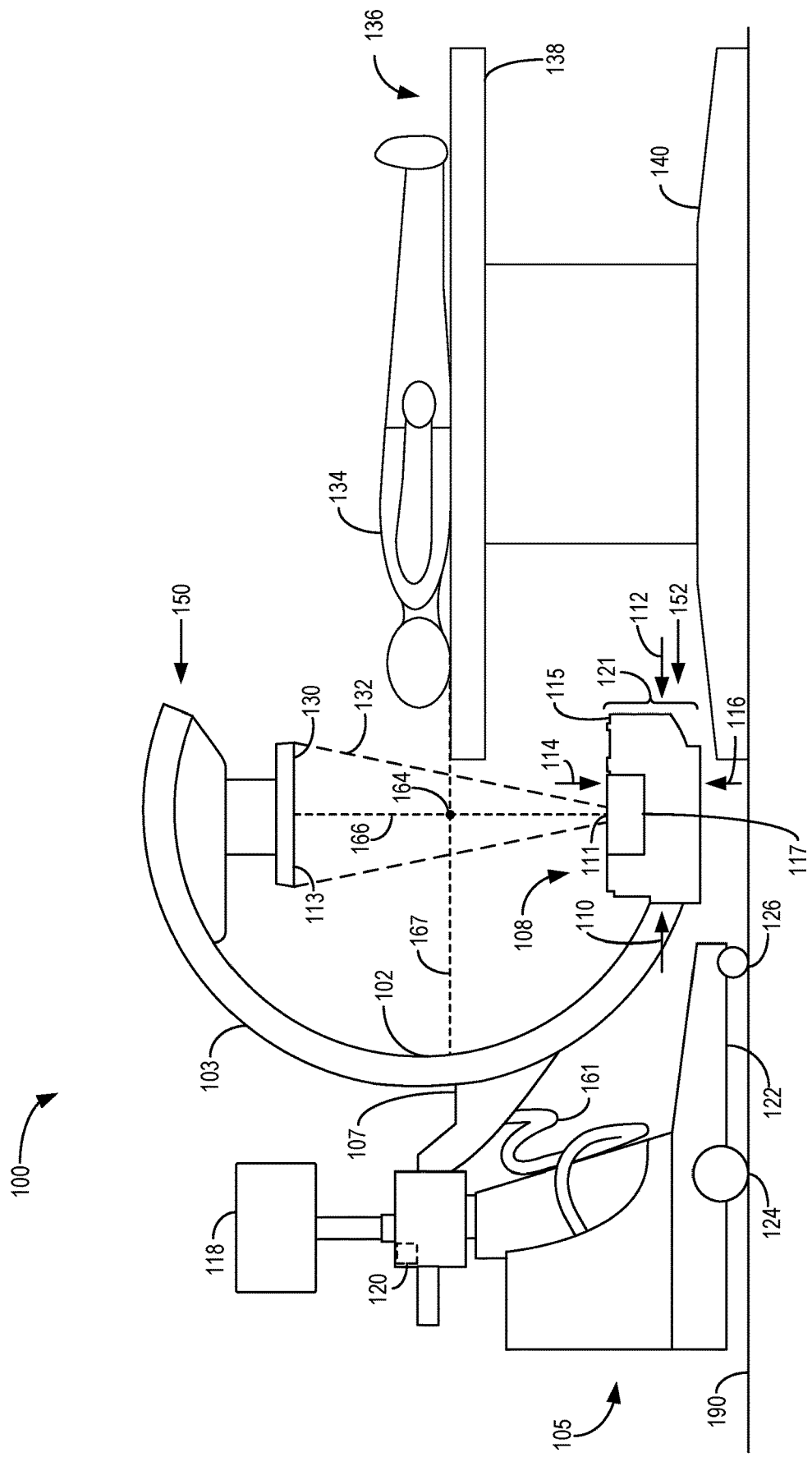
FIG. 1 shows an example medical imaging system including a C-arm with a modular imaging assembly, according to an embodiment.

Referring to FIG. 1, an imaging system 100 including a C-arm 102 with a modular imaging assembly 108 is schematically shown. The modular imaging assembly 108 may be referred to herein as an x-ray assembly and/or modular assembly. The imaging system 100 includes a radiation source, and in the examples described herein, the radiation source is a modular imaging assembly 108 positioned opposite to x-ray detector 130 and configured to emit x-ray radiation. In other examples, the radiation source may be configured to emit a different type of radiation for imaging (e.g., imaging a subject, such as patient 134), such as gamma rays, and the detector (e.g., x-ray detector 130) may be configured to detect the radiation emitted by the radiation source (e.g., x-ray beam 132). The imaging system 100 additionally includes base unit 105 supporting imaging system 100 on ground surface 190 on which the imaging system 100 sits (e.g., via base 122 supported by wheel 124, wheel 126, etc.).

The C-arm 102 includes a C-shaped portion 103 connected to an extended portion 107, with the extended portion 107 rotatably coupled to the base unit 105. The detector 130 is coupled to the C-shaped portion 103 at a first end 150 of the C-shaped portion 103, and the modular imaging assembly 108 is coupled to the C-shaped portion 103 at an opposing, second end 152 of the C-shaped portion 103. As an example, the C-arm 102 may be configured to rotate at least 180 degrees in opposing directions relative to the base unit 105. The C-arm 102 is rotatable about at least a rotational axis 164 and may additionally rotate about axis 167. The C-shaped portion 103 may be rotated as described above in order to adjust the modular imaging assembly 108 and detector 130 (positioned on opposite ends of the C-shaped portion of the C-arm 102 along axis 166, where axis 166 intersects rotational axis 164 and extends radially relative to rotational axis 164) through a plurality of positions.

During an imaging operation, a portion of a patient's body placed in an opening formed between the modular imaging assembly 108 and detector 130, may be irradiated with radiation from the x-ray source. For example, modular imaging assembly 108 may comprise an x-ray tube insert housed within casing 115, and x-ray radiation generated by the modular imaging assembly 108 may emit from an outlet 111 of the casing 115 and may be intercepted by a detector surface 113 of the detector 130. The radiation may penetrate the portion of the patient's body being irradiated, and travel to the detector 130 where the radiation is captured. By penetrating the portion of the patient's body placed between the modular imaging assembly 108 and detector 130, an image of the patient's body is captured and relayed to an electronic controller 120 of the imaging system 100 (e.g., via an electrical connection line, such as electrically conductive cable 161). The image may be displayed via display device 118.

Patient 134 may be supported by a patient support table 136, with the patient support table 136 including a support surface 138 and base 140. In the configurations described herein, height 121 of the modular imaging assembly is reduced relative to conventional configurations. As a result, a likelihood of contact of the modular imaging assembly with the patient support table 136 may be reduced.

The base unit 105 may include the electronic controller (e.g., a control and computing unit) that processes instructions or commands sent from the user input devices during operation of the imaging system 100. The base unit 105 may also include an internal power source (not shown) that provides electrical power to operate the imaging system 100. Alternatively, the base unit 105 may be connected to an external electrical power source to power the imaging system 100. A plurality of connection lines (e.g., electrical cables, such as electrically conductive cable 161) may be provided to transmit electrical power, instructions, and/or data between the modular imaging assembly 108, detector 130, and the control and computing unit. The plurality of connection lines may transmit electrical power from the electrical power source (e.g., internal and/or external source) to the modular imaging assembly 108 and detector 130.

The C-arm 102 may be adjusted to a plurality of different positions by rotation of the C-shaped portion 103 of the C-arm 102. For example, in an initial, first position shown by FIG. 1, the detector 130 may be positioned vertically above the modular imaging assembly 108 relative to a ground surface 190 on which the imaging system 100 sits, with axis 166 arranged normal to the ground surface 190 intersecting a midpoint of each of the outlet 111 of modular imaging assembly 108 and detector surface 113 of detector 130. The C-arm 102 may be adjusted from the first position to a different, second position by rotating the C-shaped portion 103. In one example, the second position may be a position in which the modular imaging assembly 108 and detector 130 are rotated 180 degrees together relative to the first position, such that the modular imaging assembly 108 is positioned vertically above the detector 130, with axis 166 intersecting the midpoint of the outlet 111 of the modular imaging assembly 108 and the midpoint of the detector surface 113 of the detector 130. When adjusted to the second position, the modular imaging assembly 108 may be positioned vertically above the rotational axis 164 of the C-shaped portion 103 of the C-arm 102, and the detector 130 may be positioned vertically below the rotational axis 164. Different rotational positions of the C-arm 102 are possible.

As described above, the imaging system 100 includes modular imaging assembly 108 positioned across rotational axis 164 relative to the detector 130. In the example shown by FIG. 1, detector 130 is positioned at a first end 150 of the C-shaped portion 103, and modular imaging assembly 108 is positioned at an opposing, second end 152 of the C-shaped portion 103. A first end 110 of the modular imaging assembly 108 is coupled to the C-shaped portion 103, with a second end 112 of the modular imaging assembly 108 arranged opposite to the first end 110. An upper end 114 of the modular imaging assembly 108 is arranged facing the detector 130, with a lower end 116 arranged opposite to the upper end 114.

Similar to the examples described below FIGS. 2-6, the modular imaging assembly 108 includes collimator 117 recessed against casing 115 (e.g., seated against a recessed surface of casing 115). In this configuration, the collimator 117 is arranged between opposing components of the modular imaging assembly 108. For example, the collimator 117 may be arranged between (e.g., flanked by) a first transformer (e.g., filament transformer) and a second transformer (e.g., high-voltage transformer), where the first transformer and second transformer are disposed within an interior of the casing 115 and the collimator 117 is arranged external to the casing 115.

By recessing the collimator 117, the height of the modular imaging assembly 108 may be reduced relative to conventional configurations. The reduced height of the modular imaging assembly 108 may increase an amount of open space between the detector surface 113 and the outlet 111 of the modular imaging assembly 108, which may enable the C-arm 102 to accommodate larger patients for imaging and/or increase an ease of use of the C-arm 102 (e.g., increase an operating clearance of the C-arm 102). Additionally, by configuring the collimator 117 to seat between the first transformer and the second transformer, a heat dissipation of the transformers may be increased relative to configurations that do not include the collimator in the recessed configuration. As a result, a durability of the C-arm 102 may be increased and a likelihood of degradation of the C-arm 102 may be reduced.

Figure 2:
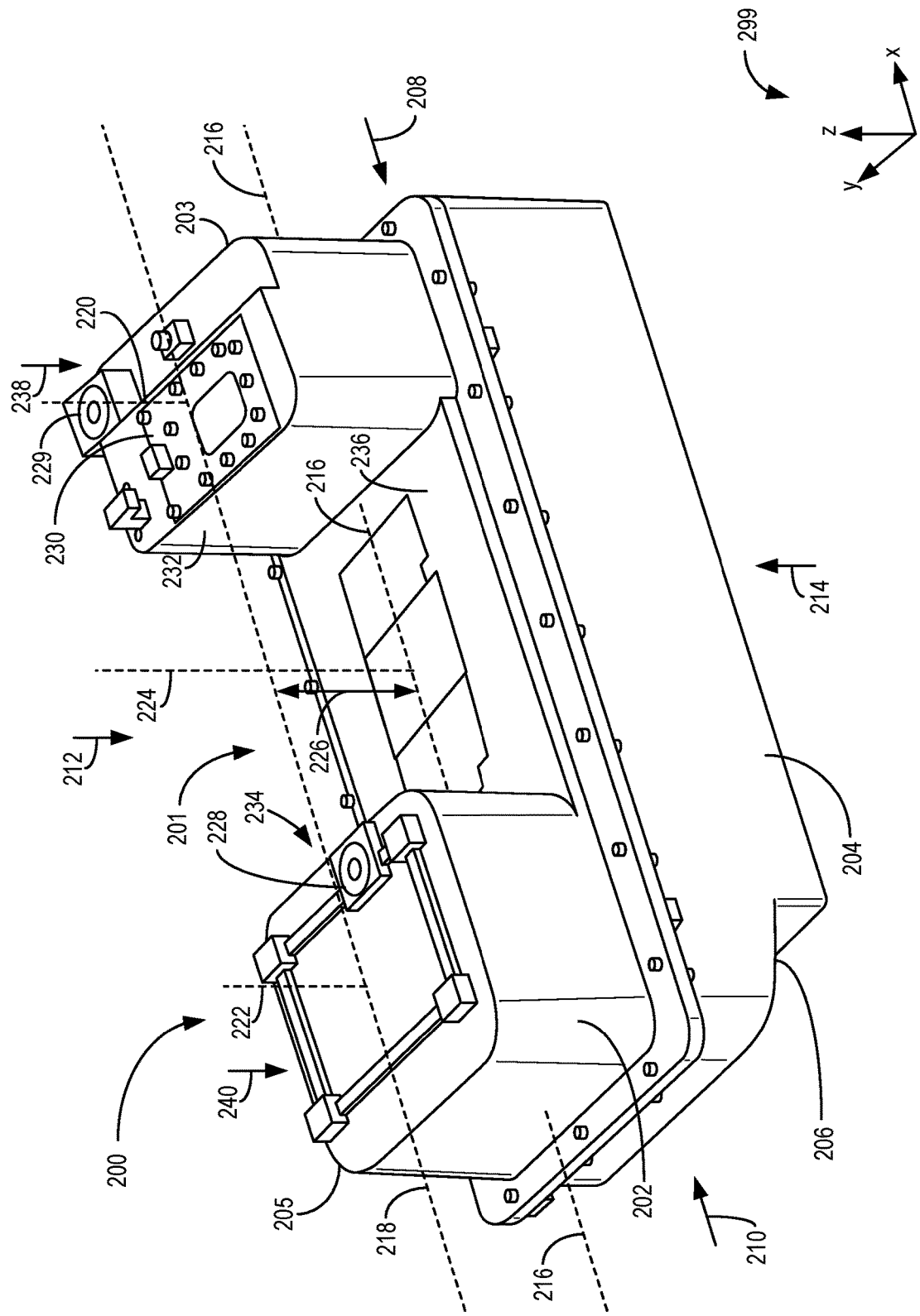
FIG. 2 shows a perspective view of a modular imaging assembly for a C-arm, according to an embodiment.

Referring to FIG. 2, a perspective view of a modular imaging assembly 200 for a C-arm (e.g., C-arm 102 shown by FIG. 1 and described above) is shown. FIG. 5 shows the modular imaging assembly 200 with a collimator 600 of the modular imaging assembly 200 seated in a recessed configuration, while in FIGS. 2-5 the modular imaging assembly 200 is shown with the collimator 600 removed. FIGS. 2-6 include references axes 299 for purposes of comparison.

Casing 206 of the modular imaging assembly 108 forms a first extension 203 housing a first component (e.g., a first transformer, as described further below) and a second extension 205 housing a second component (e.g., a second transformer, as described further below). The first extension 203 is arranged opposite to the second extension 205, with the first extension 203 and second extension 205 in the direction of upper end 212 of the modular imaging assembly 200 (e.g., with first extension 203 extending along axis 220 and with second extension 205 extending along axis 222, where axis 220 and axis 222 are parallel with each other). In particular, the first extension 203 is arranged toward a first end 208 of the modular imaging assembly 200, where the first end 208 is mounted to the C-arm of the imaging system (e.g., imaging system 100 described above with reference to FIG. 1), and the second extension 205 is arranged at a second end 210 of the modular imaging assembly 200, opposite to the first end 208.

A clearance 201 is formed between the first extension 203 and the second extension 205. As shown by FIG. 6 and described further below, collimator 600 of the modular imaging assembly 200 is shaped to seat within the clearance 201.

The casing 206 may include an upper section 202 forming the first extension 203 and the second extension 205. The casing 206 may further include a lower section 204 shaped to house an x-ray tube insert (as described further below with reference to FIG. 4), with the lower section 204 arranged at lower end 214 opposite to the upper end 212. The upper section 202 and the lower section 204 may be removably couplable to each other (e.g., the lower section 204 may couple to the upper section 202 in a configuration in which the lower section 204 is removable from the upper section 202). For example, the lower section 204 may couple to the upper section 202 via a plurality of fasteners (e.g., bolts).

In some examples, the modular imaging assembly 200 includes one or more ports configured to receive a lubricant (e.g., oil). The lubricant may increase a cooling of one or more components of the modular imaging assembly 200 (e.g., transformers, as described below). As one example, the modular imaging assembly 200 includes a first oil plug 228 and a second oil plug 229, where each oil plug seals a respective lubrication port. The modular imaging assembly 200 may further include a seal board 230 configured to seal casing 206 at the upper end 212.

Referring to FIG. 3, a side view of the modular imaging assembly 200 is shown with the collimator 600 removed.

The clearance 201 is defined by a first surface 232 of the first extension 203 and a second surface 234 of the second extension 205, where the first surface 232 faces the second extension 205 and the second surface 234 faces the first extension 203. The first surface 232 and the second surface 234 may be parallel with each other and may be perpendicular to a recessed surface 236 (which may be referred to herein as a support surface) on which the collimator 600 sits (e.g., at least a portion of collimator 600 may be arranged in face-sharing contact with the recessed surface 236, with no other components arranged therebetween). The recessed surface 236 joins the first surface 232 with the second surface 234 and forms a closed end 302 of the clearance 201, with open end 300 arranged opposite to the closed end 302. The recessed surface 236 is shaped to support the collimator 600 between the first extension 203 and the second extension 205 (e.g., between the first component housed within the first extension 203 and the second component housed within the second extension 205).

Referring to FIG. 4, a cross-sectional view of the modular imaging assembly 200 is shown with the collimator 600 removed.

As described above, the first extension 203 houses a first component (which may be referred to herein as a first modular component) and the second extension 205 houses a second component (which may be referred to herein as a second modular component). In particular, the first extension 203 forms a first component chamber 481 defined by walls 482 of the first extension 203, and the second extension 205 forms a second component chamber 483 defined by walls 484 of the second extension 205. The first component is arranged within the first component chamber 481 and is enclosed by the first extension 203, and the second component is arranged within the second component chamber 483 and is enclosed by the second extension 205. The first extension 203 and the second extension 205 each extend away from the lower section 204 and outward in a normal direction from an interface 485 joining an open end 486 of the upper section 202 with an open end 487 of the lower section 204 (e.g., first extension 203 extends outward in a direction of axis 220 and second extension 205 extends in a direction of axis 222, where axis 220 and axis 222 are parallel with each other).

An interior 438 of the casing 206 is defined at least in part by the first component chamber 481 and the second component chamber 483 (e.g., the first component chamber 481 and second component chamber 483 are formed within the interior of the upper section 202 and are not external to the upper section 202). The first component chamber 481 and the second component chamber 483 are each open at the open end 486 of the upper section 202, with the first component chamber 481 closed at terminating end 238 of the first extension 203 and with the second component chamber 483 closed at terminating end 240 of the second extension.

The interface 485 is a joint (e.g., junction) at which an interfacing surface 510 of the upper section 202 is arranged in face-sharing contact with a counterpart interfacing surface 512 of the lower section 204. In the example shown, the interfacing surface 510 is a rim surface arranged along an outer perimeter of the upper section 202, and the counterpart interfacing surface 512 is a rim surface arranged along an outer perimeter of the lower section 204. During conditions in which the interfacing surface 510 and counterpart interfacing surface 512 are in direct, face-sharing contact (e.g., directly contacting each other without other components separating the interfacing surface 510 and the counterpart interfacing surface 512), the upper section 202 and lower section 204 may be coupled together at interface 485 (e.g., via fasteners such as bolts, clips, etc.).

In the example shown, the first extension 203 houses first transformer 400 and the second extension 205 houses second transformer 402. The first transformer 400 may be referred to herein as a filament transformer and the second transformer 402 may be referred to herein as a high-voltage transformer. The filament transformer may energize a filament of x-ray tube insert 408 at a first, lower voltage (e.g., 10 volts) in order to heat the filament, and the high-voltage transformer may energize the x-ray tube insert 408 at a second, higher voltage (e.g., 40 kilovolts) to generate x-ray radiation via the x-ray tube insert 408. In some examples, the second transformer 402 may be the filament transformer and the first transformer 400 may be the high-voltage transformer.

The modular imaging assembly 200 includes a first mount 426 configured to support the first component housed within the first extension 203 (e.g., the first transformer 400) and a second mount 428 configured to support the second component housed within the second extension 205 (e.g., the second transformer 402). The first transformer 400 may couple directly to the first mount 426 (e.g., via fasteners, such as bolts) and may be maintained in position by the first mount 426. The second transformer 402 may couple directly to the second mount 428 and may be maintained in position by the second mount 428. The first mount 426 and the second mount 428 are spaced apart by length 432 extending parallel relative to central axis 420 of the x-ray tube insert 408 during conditions in which the x-ray tube insert 408 is seated within the casing 206 (e.g., as shown by FIG. 4). In this configuration, during conditions in which the first transformer 400 is coupled to the first mount 426 and the second transformer 402 is coupled to the second mount 428, the first transformer 400 is in alignment with the second transformer 402 (e.g., the first transformer 400 and the second transformer 402 are each aligned with each other along axis 216 parallel with the central axis 420 of the x-ray tube insert 408 during conditions in which the x-ray tube insert 408 is seated within the casing 206).

The modular imaging assembly 200 further includes a third mount 430 shaped to couple the modular imaging assembly 200 to the C-arm of the imaging system (e.g., C-arm 102 of imaging system 100 described above with reference to FIG. 1). As one example, the third mount 430 may be formed by the casing 206 and may couple directly to the C-arm via fasteners (e.g., bolts). Bellows 404 may be arranged adjacent to the third mount 430. The first extension 203 and the second extension 205 are arranged such that the first extension 203 is closer to the third mount 430 (e.g., closer to the C-arm during conditions in which the modular imaging assembly 200 is coupled to the C-arm) and the second extension 205 is further from the third mount 430 (e.g., further from the C-arm, as compared to the first extension 203, during conditions in which the modular imaging assembly 200 is coupled to the C-arm). In particular, the first mount 426 is arranged a length 434 from the third mount 430 and the second mount 428 is arranged a length 436 from the third mount 430, where the length 436 is greater than the length 434.

The modular imaging assembly 200 includes an x-ray tube insert 408 housed within casing 206. The x-ray tube insert 408 extends in a direction perpendicular to each of the first extension 203 and the second extension 205. In particular, a central axis 420 of the x-ray tube insert 408 is arranged perpendicular to an axis 224 extending between the x-ray tube insert 408 and a detector of an imaging system to which the modular imaging assembly 200 is mounted. The central axis 420 is normal to the first end 208 of the modular imaging assembly 200 and is spaced apart from the first transformer 400 and the second transformer 402 in a direction away from the detector (e.g., toward bottom surface 306 of the casing 206). The detector and the imaging system may be similar to, or the same as, the detector 130 and the imaging system 100, respectively, described above with reference to FIG. 1.

The x-ray tube insert 408 is arranged toward bottom surface 306 of the casing 206 and is seated (e.g., mounted) within interior 438 of the casing 206. The x-ray tube insert 408 is seated within the casing 206 in a position further from the detector compared to each of the first transformer 400, the second transformer 402, and the collimator 600 (e.g., the x-ray tube insert 408 is arranged closest to the bottom surface 306 relative to the first transformer 400, the second transformer 402, and the collimator 600). In particular, the x-ray tube insert 408 is arranged directly below the collimator 600 in a direction from the detector to the bottom surface 306 of the casing 206. In the configuration described herein, the height of the modular imaging assembly 200 (e.g., the length 310 between the bottom surface 306 and terminating end 238 of the first extension, and length 312 between the bottom surface 306 and terminating end 240 of the second extension) is reduced relative to conventional imaging assemblies. The particular configuration provides collimator 600 (shown by FIG. 5) to be recessed away from the detector and toward the bottom surface 306, with the collimator 600 arranged between the first extension 203 and the second extension 205. In this configuration, a length 414 from the bottom surface 306 to the x-ray tube insert 408 is less than each of a length 416 from the bottom surface 306 to the first transformer 400 and a length 418 from the bottom surface 306 to the second transformer 402.

The recessed surface 236 includes an aperture 406 shaped to align with an inlet 602 formed in an inlet end 604 of the collimator 600 (with the inlet 602, inlet end 604, and collimator 600 shown by FIG. 6). A length between the aperture 406 and the third mount 430 is less than the length 436 and greater than the length 434. During conditions in which the x-ray tube insert 408 is seated within the casing 206, the aperture 406 is aligned with outlet 440 of the x-ray tube insert 408, where outlet 440 is an x-ray emission outlet of the x-ray tube insert 408 (e.g., x-ray radiation is emitted from the x-ray tube insert 408 in the direction of the detector of the imaging system at outlet 440). In this configuration, x-ray radiation output by the x-ray tube insert 408 passes through the collimator 600 between the first transformer 400 and the second transformer 402.

The recessed surface 236 separates the collimator 600 from the x-ray tube insert 408 such that the x-ray tube insert 408 is arranged within the interior 438 of the casing 206 and the collimator 600 is arranged exterior to the casing 206 (e.g., outside of interior 438 and separated from interior 438 by the recessed surface 236). In particular, the collimator 600 is supported by the recessed surface 236 and is offset by length 410 from the x-ray tube insert 408 by the recessed surface 236 in a direction of radiation emission from the x-ray tube insert 408 (e.g., the direction of axis 224, where axis extends toward the detector of the C-arm, such as detector 130 of C-arm 102 described above with reference to FIG. 1).

In some examples, the modular imaging assembly 200 may include an insulating cover 422 configured to insulate the electrical components of the modular imaging assembly 200 from each other (e.g., electrically isolate high-voltage board 424 from casing 206).

Referring to FIG. 5, an exploded view of the modular imaging assembly 200 is shown. The modular imaging assembly 200 includes a plurality of modular components configured to seat in alignment with each other during assembly of the modular imaging assembly 200, such as the collimator 600 shown by FIG. 6 and described above. In particular, the modular imaging assembly 200 includes first transformer 400, second transformer 402, collimator 600 (shown by FIG. 6), and x-ray tube insert 408. The casing 206 of the modular imaging assembly 200 is configured such that the modular components described above may be easily seated within the casing 206 in a pre-determined aligned configuration (e.g., with the first transformer 400 in substantially alignment with the second transformer 402 and with the collimator 600 arranged between the first transformer 400 and the second transformer 402).

As one example, the modular components may be coupled to the casing 206 by inserting the modular components into the casing 206 and into direct, face-sharing contact with the respective surfaces of the casing 206 (e.g., first transformer 400 may be seated in direct contact with first mount 426 shown by FIG. 5, second transformer 402 may be seated in direct contact with second mount 428, and collimator 600 may be seated in direct contact with recessed surface 236). In some examples, the modular components may include protrusions or other features configured to engage with counterpart features of the surfaces of the casing 206 (e.g., first mount 426 may include counterpart features such as indentations shaped to receive protrusions of the first transformer 400, second mount 428 may include protrusions shaped to engage with counterpart grooves, indentations, etc., of the second transformer 402, etc.).

In some examples, the modular imaging assembly 200 may include one or more filters configured to filter a portion of x-ray radiation emitted by the x-ray tube insert 408. For example, a first filter 500 may be included to reduce scattering of x-ray radiation.

Referring to FIG. 6, a cross-sectional view of the modular imaging assembly 200 is shown with the collimator 600 in a recessed configuration. The collimator is seated within the clearance 201, where the clearance 201 is formed between the first extension 203 and the second extension 205 and is exterior to the casing 206 (e.g., the clearance 201 is outside of the casing 206 and is not within interior 438 of the casing 206).

An outlet end 606 of collimator 600 is substantially aligned with terminating end 238 of the first extension 203 and terminating end 240 of the second extension 205. During operation of the modular imaging assembly 200, uncollimated (e.g., multi-directional) x-ray radiation may be generated by the x-ray tube insert 408 and may pass through the aperture 406 to the collimator 600. The collimator 600 may collimate the x-ray radiation by allowing x-ray radiation of a particular direction (e.g., orientation) to pass through the collimator to the outlet end 606 (e.g., to outlet 607). The collimated x-ray radiation may then pass to the detector arranged opposite to the modular imaging assembly 200 (e.g., arranged at an end of the C-arm opposite to the end at which the modular imaging assembly 200 is coupled) and may be intercepted by the detector (e.g., in order to form an image of the subject to be imaged by the imaging system).

The terminating end 238 is a closed end of the first extension 203 arranged opposite to the lower section 204 (e.g., extending away from bottom surface 306 shown by FIG. 3), and the terminating end 240 is a closed end of the second extension 205 arranged opposite to the lower section 204. The terminating end 238 and the terminating end 240 may be substantially aligned (e.g., substantially arranged along a same axis or plane). For example, length 310 between the bottom surface 306 and the terminating end 238 may be the same as (e.g., equal to) length 312 between the bottom surface 306 and the terminating end 240. "Substantial alignment" of the terminating end 238 and the terminating end 240 refers to alignment of the ends along a same axis or plane (e.g., axis 218 extending parallel with axis 308, where axis 308 is parallel with the bottom surface 306 and arranged along the bottom surface 306). For example, terminating end 238 and terminating end 240 may each be arranged along axis 218, where axis 218 is parallel with the central axis 420 of the x-ray tube insert 408.

During conditions in which the collimator 600 is seated within the clearance 201 (as shown by FIG. 6), the inlet 602 of the collimator 600 is arranged such that length 412 between the inlet and the x-ray tube insert 408 is less than a length 226 between the recessed surface 236 and either of the terminating end 238 of the first extension 203 or the terminating end 240 of the second extension 205. Further, length 412 from bottom surface 306 of the casing 206 to the inlet 602 is less than length 304 (shown by FIGS. 3-4) of the clearance 201 between the first extension 203 and the second extension 205. The length 412 is the length from the bottom surface 306 to the inlet 602 as well as the length from the bottom surface 306 to the aperture 406 (e.g., the inlet 602 and the aperture 406 may be arranged directly adjacent to each other with no other components therebetween).

In this configuration, the collimator 600 is supported by the recessed surface 236 substantially equidistant from the first component housed within the first extension 203 (e.g., first transformer 400) and the second component housed within the second extension 205 (e.g., second transformer 402) in a direction parallel to the central axis of the x-ray tube insert 408 while the x-ray tube insert 408 is seated within the casing 206. In particular, a length 605 between the collimator 600 and the first transformer 400 as shown by FIG. 6 may be substantially equal to a length 608 between the collimator 600 and the second transformer 402 (e.g., the length 605 may be within a range of +/−5% the length 608).

The recessed surface 236 is recessed away from an upper surface 442 of the first transformer 400 and an upper surface 444 of the second transformer 402. While the collimator 600 is supported by the recessed surface 236 (e.g., seated directly against the recessed surface 236), the collimator 600 is substantially aligned with the upper surface 442 of the first transformer 400 and the upper surface 444 of the second transformer 402. Length 446 between bottom surface 306 and the upper surface 442 of the first transformer 400 is at least 80% of length 610 between the bottom surface 306 and upper surface 612 of the collimator 600. Similarly, length 448 between bottom surface 306 and the upper surface 444 of the second transformer 402 is at least 80% of length 610 between the bottom surface 306 and the upper surface 612 of the collimator 600. In some examples, the length 446 and/or the length 448 may be 90% of the length 610. In some examples, the length 446 and/or the length 448 may be 95% of the length 610. In yet other examples, the length 446 and/or the length 448 may be equal to the length 610.

By configuring the modular imaging assembly 200 as described above with the collimator 600 in the recessed configuration between the first transformer 400 and the second transformer 402, the size of the modular imaging assembly 200 may be reduced. Further, by configuring the first transformer 400 and the second transformer 402 to be seated at opposing ends of the modular imaging assembly 200, a heat dissipation (e.g., cooling) of the first transformer 400 and/or second transformer 402 may be increased, which may increase a performance of the imaging system. The modular configuration of the components of the modular imaging assembly may reduce an assembly time of the modular imaging assembly and/or reduce a production cost of the modular imaging assembly.

FIGS. 2-6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The disclosure also provides support for an assembly for a C-arm, comprising: a casing including a first extension housing a first component, a second extension housing a second component, and a clearance formed between the first extension and the second extension, and a collimator seated within the clearance, with an outlet end of the collimator substantially aligned with a terminating end of the first extension and a terminating end of the second extension. In a first example of the system, the first component is a filament transformer and the second component is a high-voltage transformer. In a second example of the system, optionally including the first example, the system further comprises: an x-ray tube insert housed within the casing and extending perpendicular to the first extension and the second extension. In a third example of the system, optionally including one or both of the first and second examples, a length from a bottom surface of the casing to the x-ray tube insert is less than each of a length from the bottom surface to the first component and a length from the bottom surface to the second component. In a fourth example of the system, optionally including one or more or each of the first through third examples, the x-ray tube insert is arranged between the first component and the second component within an interior of the casing and the collimator is arranged between the first component and the second component within the clearance at an exterior of the casing. In a fifth example of the system, optionally including one or more or each of the first through fourth examples: the casing includes an upper section forming the first extension and the second extension, and a lower section housing the x-ray tube insert and shaped to removably couple with the upper section; the first extension and the second extension each extend away from the lower section and outward in a normal direction from an interface joining an open end of the upper section with an open end of the lower section; an interior of the upper section is defined at least by a first component chamber formed within the first extension by walls of the first extension and a second component chamber formed within the second extension by walls of the second extension; the first component chamber and the second component chamber are each open at the open end of the upper section; the first component chamber is closed at the terminating end of the first extension; and the second component chamber is closed at the terminating end of the second extension. In a sixth example of the system, optionally including one or more or each of the first through fifth examples, the clearance is defined by a first surface of the first extension facing the second extension, a second surface of the second extension facing the first extension, and a recessed surface joining the first surface to the second surface, where the first surface and the second surface are parallel to each other and perpendicular to the recessed surface. In a seventh example of the system, optionally including one or more or each of the first through sixth examples, the recessed surface includes an aperture shaped to align with an inlet formed in an inlet end of the collimator. In a eighth example of the system, optionally including one or more or each of the first through seventh examples, a length between the inlet and the x-ray tube insert is less than a length between the recessed surface and either of the terminating end of the first extension or the terminating end of the second extension. In a ninth example of the system, optionally including one or more or each of the first through eighth examples, a length from a bottom surface of the casing to the inlet is less than a length of the clearance between the first extension and the second extension.

The disclosure also provides support for a modular assembly for a C-arm, comprising: a first mount shaped to support a first modular component, a second mount spaced apart from the first mount and shaped to support a second modular component in alignment with the first modular component, and a support surface shaped to support a collimator between the first modular component and the second modular component and offset from an x-ray tube insert. In a first example of the system, the support surface is shaped to support the collimator offset from the x-ray tube insert in a direction of radiation emission of the x-ray tube insert. In a second example of the system, optionally including the first example, the support surface is shaped to support the collimator substantially equidistant to the first modular component and the second modular component in a direction parallel to a central axis of the x-ray tube insert. In a third example of the system, optionally including one or both of the first and second examples, the system further comprises: a third mount shaped to couple the modular assembly to the C-arm, where the first mount is arranged a first length from the third mount, an aperture of the support surface aligned with an outlet of the x-ray tube insert is arranged a second length from the third mount, the second mount is arranged a third length from the third mount, and none of the first length, the second length, and the third length are equal. In a fourth example of the system, optionally including one or more or each of the first through third examples, the first length is smaller than the second length, the second length is smaller than the third length, and the first length, the second length, and the third length are parallel with a central axis of the x-ray tube insert.

The disclosure also provides support for an imaging system, comprising: a c-arm, an x-ray detector, an x-ray assembly mounted at a first end to the c-arm and opposite to the x-ray detector, including: a first transformer arranged toward the first end, a second transformer arranged at a second end opposite to the first end, and a collimator arranged between the first transformer and the second transformer and seated against a support surface recessed away from an upper surface of the first transformer and an upper surface of the second transformer. In a first example of the system, the system further comprises: an x-ray tube insert aligned with the collimator and arranged further from the detector than each of the first transformer, the second transformer, and the collimator. In a second example of the system, optionally including the first example, the collimator is substantially aligned with the upper surface of the first transformer and the upper surface of the second transformer. In a third example of the system, optionally including one or both of the first and second examples, a direction of x-ray radiation output by the x-ray tube insert is between the first transformer and the second transformer and through the collimator. In a fourth example of the system, optionally including one or more or each of the first through third examples, a central axis of the x-ray tube insert is normal to the first end and is spaced apart from the first transformer and the second transformer in a direction away from the detector, and a length between a bottom surface of the x-ray assembly and the upper surface of the first transformer or the upper surface of the second transformer is at least 80% of a length between the bottom surface and an upper surface of the collimator.

As used herein, the term "approximately" is construed to mean plus or minus five percent of the range unless otherwise specified.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An assembly for a C-arm, comprising:
a casing including a first extension housing a first component, a second extension housing a second component, and a clearance formed between the first extension and the second extension; and
a collimator seated within the clearance, with an outlet end of the collimator substantially aligned with a terminating end of the first extension and a terminating end of the second extension.

2. The assembly of claim 1, wherein the first component is a filament transformer and the second component is a high-voltage transformer.

3. The assembly of claim 1, further comprising an x-ray tube insert housed within the casing and extending perpendicular to the first extension and the second extension.

4. The assembly of claim 3, wherein a length from a bottom surface of the casing to the x-ray tube insert is less than each of a length from the bottom surface to the first component and a length from the bottom surface to the second component.

5. The assembly of claim 3, wherein the x-ray tube insert is arranged between the first component and the second component within an interior of the casing and the collimator is arranged between the first component and the second component within the clearance at an exterior of the casing.

6. The assembly of claim 3, wherein:
the casing includes an upper section forming the first extension and the second extension, and a lower section housing the x-ray tube insert and shaped to removably couple with the upper section;

the first extension and the second extension each extend away from the lower section and outward in a normal direction from an interface joining an open end of the upper section with an open end of the lower section;

an interior of the upper section is defined at least by a first component chamber formed within the first extension by walls of the first extension and a second component chamber formed within the second extension by walls of the second extension;

the first component chamber and the second component chamber are each open at the open end of the upper section;

the first component chamber is closed at the terminating end of the first extension; and the second component chamber is closed at the terminating end of the second extension.

7. The assembly of claim 3, wherein the clearance is defined by a first surface of the first extension facing the second extension, a second surface of the second extension facing the first extension, and a recessed surface joining the first surface to the second surface, where the first surface and the second surface are parallel to each other and perpendicular to the recessed surface.

8. The assembly of claim 7, wherein the recessed surface includes an aperture shaped to align with an inlet formed in an inlet end of the collimator.

9. The assembly of claim 8, wherein a length between the inlet and the x-ray tube insert is less than a length between the recessed surface and either of the terminating end of the first extension or the terminating end of the second extension.

10. The assembly of claim 8, wherein a length from a bottom surface of the casing to the inlet is less than a length of the clearance between the first extension and the second extension.

11. A modular assembly for a C-arm, comprising:
a first mount shaped to support a first modular component;
a second mount spaced apart from the first mount and shaped to support a second modular component in alignment with the first modular component; and
a support surface shaped to support a collimator between the first modular component and the second modular component and offset from an x-ray tube insert.

12. The modular assembly of claim 11, wherein the support surface is shaped to support the collimator offset from the x-ray tube insert in a direction of radiation emission of the x-ray tube insert.

13. The modular assembly of claim 11, wherein the support surface is shaped to support the collimator substantially equidistant to the first modular component and the second modular component in a direction parallel to a central axis of the x-ray tube insert.

14. The modular assembly of claim 11, further comprising a third mount shaped to couple the modular assembly to the C-arm, where the first mount is arranged a first length from the third mount, an aperture of the support surface aligned with an outlet of the x-ray tube insert is arranged a second length from the third mount, the second mount is arranged a third length from the third mount, and none of the first length, the second length, and the third length are equal.

15. The modular assembly of claim 14, wherein the first length is smaller than the second length, the second length is smaller than the third length, and the first length, the second length, and the third length are parallel with a central axis of the x-ray tube insert.

16. An imaging system, comprising:
a c-arm;
an x-ray detector;
an x-ray assembly mounted at a first end to the c-arm and opposite to the x-ray detector, including:
a first transformer arranged toward the first end;
a second transformer arranged at a second end opposite to the first end; and
a collimator arranged between the first transformer and the second transformer and seated against a support surface recessed away from an upper surface of the first transformer and an upper surface of the second transformer.

17. The imaging system of claim 16, further comprising an x-ray tube insert aligned with the collimator and arranged further from the detector than each of the first transformer, the second transformer, and the collimator.

18. The imaging system of claim 16, wherein the collimator is substantially aligned with the upper surface of the first transformer and the upper surface of the second transformer.

19. The imaging system of claim 17, wherein a direction of x-ray radiation output by the x-ray tube insert is between the first transformer and the second transformer and through the collimator.

20. The imaging system of claim 17, wherein a central axis of the x-ray tube insert is normal to the first end and is spaced apart from the first transformer and the second transformer in a direction away from the detector, and a length between a bottom surface of the x-ray assembly and the upper surface of the first transformer or the upper surface of the second transformer is at least 80% of a length between the bottom surface and an upper surface of the collimator.

* * * * *